United States Patent [19]

Emerson et al.

[11] Patent Number: 5,670,147

[45] Date of Patent: *Sep. 23, 1997

[54] COMPOSITIONS CONTAINING CULTURED MITOTIC HUMAN STEM CELLS

[75] Inventors: Stephen G. Emerson; Michael F. Clarke; Bernhard O. Palsson, all of Ann Arbor, Mich.

[73] Assignee: Regents of the University of Michigan, Ann Arbor, Mich.

[*] Notice: The portion of the term of this patent subsequent to Nov. 2, 2014, has been disclaimed.

[21] Appl. No.: 352,198

[22] Filed: Dec. 1, 1994

Related U.S. Application Data

[60] Continuation of Ser. No. 143,751, Nov. 1, 1993, abandoned, which is a division of Ser. No. 737,024, Jul. 29, 1991, abandoned, which is a continuation-in-part of Ser. No. 628,343, filed as PCT/US90/03438, Jun. 14, 1990, abandoned, which is a continuation-in-part of Ser. No. 366,639, Jun. 15, 1989, abandoned.

[51] Int. Cl.$^6$ .............................. C12N 5/00; A01N 63/00
[52] U.S. Cl. ...................... 424/93.1; 424/93.3; 435/240.2
[58] Field of Search ........................... 424/937; 435/240.2

[56] References Cited

U.S. PATENT DOCUMENTS 5,199,942  4/1993  Gules ............................................ 604/4

FOREIGN PATENT DOCUMENTS 2062741  12/1990  Canada.
WO95/06409  3/1995  WIPO.

OTHER PUBLICATIONS

Gail K. Naughton, et al.; Journal of Cellular Biochemistry; Hematopoeisis on Nylon Mesh Microenvironments; 19th Annual Meeting (1990).

Jerry Caldwell, et al.; Biotechnology Progress; Influence of Medium Exchange Schedules on Metabolic, Growth, and GM-CSF Secretion Rates of Genetically Engineered NIH-3T3 Cells; vol. 7; pp. 1-8; (1991).

Jerry Caldwell, et al.; Journal of Cellular Physiology; Culture Perfusion Schedules Influence the Metabolic Activity and Granulocyte-Macrophage Colony-Stimulating Factor Production Rates of Human Bone Marrow Stromal Cells; vol. 147, No. 2; pp. 344-353; (1991).

Richard M. Schwartz, et al.; Blood; In Vitro Myelopoiesis Stimulated by Rapid Medium Exchange and Supplementation With Hematopoietic Growth Factors; vol. 78, No. 12; pp. 3155-3161; (1991).

Richard M. Schwartz, et al.; Proceedings of the National Academy of Sciences; Rapid Medium Perfusion Rate Significantly Increases the Productivity and Longevity of Human Bone Marrow Cultures;; vol. 88, No. 15; pp. 6760-6764; (1991).

Faurer et al Hood 52(6):1243, 1970.
Gartner et al PNAS 77(8):4756, 1980.
Adamson et al Canada Journal of Chem Engin 64:531, 1986.
Dextr et al Nature 309:746, 1984.
Grif et al Suere 230:1171, 1985.
Mafzow et al Exp. Hemet. 18:1049, 1990.
Stephenson et al PNAS 68(7):1542, 1971.
Suda et al Blood 74(6):1936, 1989.

Primary Examiner—Suzanne E. Ziska
Attorney, Agent, or Firm—Oblon, Spivak, McClelland, Maier & Neustadt, P.C.

[57] ABSTRACT

Methods, including culture media conditions, which provide for ex vivo human stem cell division and/or the optimization of human hematopoietic progenitor cell cultures and/or increasing the metabolism or GM-CSF secretion or IL-6 secretion of human stromal cells are disclosed. The methods rely on culturing human stem cells and/or human hematopoietic progenitor cells and/or human stromal cells in a liquid culture medium which is replaced, preferably perfused, either continuously or periodically, at a rate of 1 ml of medium per ml of culture per about 24 to about 48 hour period, and removing metabolic products and replenishing depleted nutrients while maintaining the culture under physiologically acceptable conditions. Optionally growth factors are added to the culture medium.

51 Claims, No Drawings

COMPOSITIONS CONTAINING CULTURED MITOTIC HUMAN STEM CELLS

This application is a Continuation of application Ser. No. 08/143,751, filed on Nov. 1, 1993, now abandoned, which was a division of application Ser. No. 07/737,024, filed Jul. 29, 1991, abandoned, which was a continuation-in-part of application Ser. No. 07/628,343, filed Dec. 17, 1990, abandoned, which was a continuation-in-part of application Ser. No. 07/366,639, filed Jun. 15, 1989, abandoned, which was filed as International Application No. PCT/US90/03438, on Jun. 14, 1990.

BACKGROUND OF THE INVENTION

1. Field of the Invention:

This invention relates to methods and compositions for the growth of mammalian cells in culture, particularly the growth of hematopoietic cell cultures.

2. Discussion of the Background:

All of the circulating blood cells in the normal adult, including erythrocytes, leukocytes, platelets and lymphocytes, originate as precursor cells within the bone marrow. These cells, in turn, derive from very immature cells, called progenitors, which are assayed by their development into contiguous colonies of mature blood cells in 1–3 week cultures in semisolid media such as methylcellulose or agar. Progenitor cells themselves derive from a class of progenitor cells called stem cells. Stem cells have the capacity, upon division, for both self-renewal and differentiation into progenitors. Thus, dividing stem cells generate both additional primitive stem cells and somewhat more differentiated progenitor cells. In addition to the generation of blood cells, stem cells also may give rise to osteoblasts and osteoclasts, and perhaps cells of other tissues as well. This document described methods and compositions which permit, for the first time, the successful in vitro culture of human hematopoietic stem cells, which results in their proliferation and differentiation into progenitor cells and more mature blood cells.

In the late 1970s the liquid culture system was developed for growing hematopoietic bone marrow in vitro. The cultures are of great potential value both for the analysis of normal and leukemic hematopoiesis and for the experimental manipulation of bone marrow, for, e.g., retroviral-mediated gene transfer. These cultures have allowed a detailed analysis of murine hematopoiesis and have resulted in a detailed understanding of the murine system. In addition, it has made possible retroviral gene transfer into cultured mouse bone marrow cells. This allowed tagging murine hematopoietic cells proving the existence of the multi-potent stem cell and of the study of the various genes in the process of leukemogenesis.

But while it has been possible to transfer retroviral genes into cultured mouse bone marrow cells, this is not yet been possible in cultured human bone marrow cells because, to date, human long-term bone marrow cultures have been limited both in their longevity and in their ability to maintain stem cell survival and their ability to produce progenitor cells over time.

Human liquid bone marrow cultures were initially found to have a limited hematopoietic potential, producing decreasing numbers of progenitor cells and mature blood cells, with cell production ceasing by 6 to 8 weeks. Subsequent modifications of the original system resulted only in modest improvements. A solution to this problem is of incalculable value in that it would permit, e.g., expanding human stem cells and progenitor cells for bone marrow transplantation and for protection from chemotherapy, selecting and manipulating such cells, i.e., for gene transfer, and producing mature human blood cells for transfusion therapy.

Studies of hematopoiesis and in vitro liquid marrow cultures have identified fibroblasts and endothelial cells within adhering layers as central cellular stromal elements. These cells both provide sites of attachment for developing hematopoietic cells and can be induced to secrete hematopoietic growth factors which stimulate progenitor cell proliferation and differentiation. These hematopoietic growth factors include granulocyte colony stimulating factor (G-CSF), granulocyte-macrophage colony stimulating factor (GM-CSF) and interleukin 6 (IL-6).

Cultures of human bone marrow cells on such adherent layers in vitro however have been largely disappointing. Unlike related cultures from other species, such as mouse and tree shrew, human liquid marrow cultures fail to produce significant numbers of either nonadherent hematopoietic precursor cells or clonogenic progenitor cells for over 6 to 8 weeks. And although cultures lasting 3–5 months have been reported, no culture which stably produces progenitor cells from stem cells continuously for more than 4–6 weeks has been reported.

Moreover, nonadherent and progenitor cell production typically declined throughout even the short life of these cultures, so that it is not clear that stem cell survival or proliferation is supported at all by these cultures. Further, when studied in isolation, unstimulated bone marrow stromal cells secrete little if any detectable hematopoietic growth factors (HGFs).

The lack of stable progenitor cell and mature blood cell production in these cultures has led to the belief that they are unable to support continual stem cell renewal and expansion. It has therefore been presumed that the cultures either lack a critical stem cell stimulant(s) and/or contain a novel stem cell inhibitor(s). But while explanations for failure to detect HGFs and uninduced stromal cell cultures have been suggested, the null hypothesis, which combines the failure to detect HGFs and the relative failure of human liquid marrow cultures, would be that the culture systems used in vitro do not provide the full range of hematopoietic supportive function of adherent bone marrow stromal cells in vivo.

Stem cell and progenitor cell expansion for bone marrow transplantation is a potential application for human long-term bone marrow cultures. Human autologous and allogenic bone marrow transplantation are currently used as therapies for diseases such as leukemia, lymphoma and other life-threatening disorders. For these procedures however, a large amount of donor bone marrow must be removed to insure that there is enough cells for engraftment.

A culture providing stem cell and progenitor cell expansion would reduce the need for large bone marrow donation and would make possible obtaining a small marrow donation and then expanding the number of stem cells and progenitor cells in vitro before infusion into the recipient. Also, it is known that a small number of stem cells and progenitor cells circulate in the blood stream. If these stem cells and progenitor cells could be collected by phoresis and expanded, then it would be possible to obtain the required number of stem cells and progenitor cells for transplantation from peripheral blood and eliminate the need for bone marrow donation.

Bone marrow transplantation requires that approximately $1\times10^8$ to $2\times10^8$ bone marrow mononuclear cells per kilogram of patient weight be infused for engraftment. This requires the bone marrow donation of the same number of cells which is on the order of 70 ml of marrow for a 70 kg donor. While 70 ml is a small fraction of the donors marrow, it requires an intensive donation and significant loss of blood in the donation process. If stem cells and progenitor cells could be expanded ten-fold, the donation procedure would be greatly reduced and possibly involve only collection of stem cells and progenitor cells from peripheral blood and expansion of these stem cells and progenitor cells.

Progenitor cell expansion would also be useful as a supplemental treatment to chemotherapy, and is another application for human long-term bone marrow cultures. The dilemma faced by oncologist is that most chemotherapy agents used to destroy cancer act by killing all cells going through cell division. Bone marrow is one of the most prolific tissues in the body and is therefore often the organ that is initially damaged by chemotherapy drugs. The result is that blood cell production is rapidly destroyed during chemotherapy treatment and chemotherapy must be terminated to allow the hematopoietic system to replenish the blood cell supply before a patient is retreated with chemotherapy. It may take a month or more for the once quiescent stem cells to raise up the white blood cell count to acceptable levels to resume chemotherapy during which case the drop in blood cell count is repeated. Unfortunately, while blood cells are regenerating between chemotherapy treatments, the cancer has time to grow and possibly become more resistant to the chemotherapy drugs due to natural selection.

To shorten the time between chemotherapy treatments, large numbers of progenitor and immature blood cells could be given back to the patient. This would have the effect of greatly reducing the time the patient would have low blood cell counts, thereby allowing more rapid resumption of the chemotherapy treatment. The longer chemotherapy is given and the shorter the duration between treatments, the greater the odds of successfully killing the cancer.

The hematopoietic cells required for progenitor cell expansion may come from either bone marrow withdrawal or peripheral blood collection. Bone marrow harvests would result in collection of approximately $4 \times 10^5$ CFU-GM progenitor cells. Phoresis of 5 liters of peripheral blood would collect approximately $10^5$ CFU-GM although this number could be increased to $10^6$ CFU-GM by prior treatment of the donor with GM-CSF. Rapid recovery of a patient would require transfusion of approximately $1 \times 10^8$ to $5 \times 10^8$ CFU-GM which is 100 to 1,000 times more than obtained by routine bone marrow donation or by peripheral blood donation. Therefore, expansion of bone marrow or peripheral blood to increase the number of CFU-GM 2 to 3 orders of magnitude would significantly affect chemotherapy administration and cancer treatment.

Gene therapy is a rapidly growing field in medicine which is also of inestimable clinical potential. Gene therapy is, by definition, the insertion of genes into cells for the purpose of medicinal therapy. Research in gene therapy has been on-going for several years in several types of cells in vitro and in animal studies, and has recently entered the first human clinical trials. Gene therapy has many potential uses in treating disease and has been reviewed extensively. See, e.g., *Boggs, Int. J. Cell Cloning.* (1990) 8:80–96, *Kohn et al, Cancer Invest.* (1989) 7 (2):179–192, *Lehn, Bone Marrow Transp.* (1990) 5:287–293, and *Verma, Scientific Amer.* (1990) pp. 68–84.

The human hematopoietic system is an ideal choice for gene therapy in that hematopoietic stem cells are readily accessible for treatment (bone marrow or peripheral blood harvest), they are believed to posses unlimited self-renewal capabilities (inferring lifetime therapy), and upon reinfusion, can expand and repopulate the marrow. Unfortunately, achieving therapeutic levels of gene transfer into stem cells has yet to be accomplished in humans.

Several disorders of the hematopoietic system include thalassemia, sickle cell anemia, Falconi's anemia, AIDS and SCIDS (ADA, adenosine deaminase deficiency). These candidates include both diseases that are inherited such as hemoglobinopathies and virally caused diseases of the hematopoietic system such as AIDS.

A salient problem which remain to be addressed for successful human gene therapy is the ability to insert the desired therapeutic gene into the chosen cells in a quantity such that it will be beneficial to the patient. To date, no method for doing this is available.

There is therefore a considerable need for methods and compositions for the ex vivo replication of human stem cells and for the optimization of human hematopoietic progenitor cell cultures, particularly in light of the great potential for stem cell expansion, progenitor cell expansion, and gene therapy offered by these systems. Unfortunately, to date, attempts to achieve such results have been disappointing.

SUMMARY OF THE INVENTION

Accordingly, it is an object of this invention to provide novel methods, including culture media conditions, for the ex vivo replication of human stem cells.

It is another object of this invention to provide novel methods, including culture media conditions, for the optimization of human hematopoietic progenitor cell cultures.

The present invention is based on the inventors' discovery of novel methods, including culture media conditions, which provide for ex vivo human stem cell division and/or the optimization of human hematopoietic progenitor cell cultures. These methods rely on culturing human stem cells and/or human hematopoietic progenitor cells in a liquid culture medium which is replaced, preferably perfused, either continuously or periodically, at a rate of 1 milliliter (ml) of medium per ml of culture per about 24 to about 48 hour period, and removing metabolic products and replenishing depleted nutrients while maintaining the culture under physiologically acceptable conditions. In a particularly preferred embodiment of the present invention, the above medium replacement rate is used in conjunction with the addition of hematopoietic growth factors to the rapidly exchanged culture medium.

The inventors have discovered that the increased medium exchange rate used in accordance with the present invention, with the optional addition of hematopoietic growth factors to the rapidly exchanged culture medium, surprisingly (1) supports cultures in which human stem cells proliferate over extended periods of time of at least 5 months, (2) supports cultures in which human hematopoietic progenitor cells are produced by division and differentiation of human stem cells through extended culture periods of at least 5 months, and (3) stimulates the increased metabolism of and GM-CSF secretion from human stromal cells, including human bone marrow stromal cells. The present invention provides, for the first time, human stem cell survival and proliferation in culture.

DESCRIPTION OF THE PREFERRED EMBODIMENTS

The advantages of the present invention may be observed whenever the present invention is applied to any standard system for liquid human hematopoietic culture. By the use of the rapid medium exchange rates used in accordance with the present invention, with the optional addition of supplementary hematopoietic growth factors to the culture, the inventors have surprisingly discovered that one is able to make standard systems for liquid human hematopoietic cultures, which comprise cultures performed in the presence or absence of animal sera or plasmas, including horse, calf, fetal calf, or human serum, perform in a qualitatively superior manner.

Human liquid hematopoietic cultures which may be used in accordance with the invention can be performed at cell densities of from $10^4$ to $10^9$ cells per ml of culture, using standard known medium components such as, for example, IMDM, MEM, DMEM, RPMI 1640, Alpha Medium or McCoy's Medium, which can use combinations of serum albumin, cholesterol and/or lecithin, selenium and inorganic salts. As known, these cultures may be supplemented with corticosteroids, such as hydrocortisone at a concentration of $10^{-4}$ to $10^{-7}$ M, or other corticosteroids at equal potent dose such as cortisone, dexamethasone or solumedrol. These cultures are typically carried out at a pH which is roughly physiologic, i.e. 6.9 to 7.4. The medium is typically exposed to an oxygen-containing atmosphere which contains from 4 to 20 vol. percent oxygen, preferably 6 to 8 vol. percent oxygen.

Using these standard culture techniques, the cell mass used may be enriched, by any desired amount, such as by up to $10^3$ fold or more, either for stem cell content or for hematopoietic progenitor cell content. Different known methods may be used to achieve this enrichment, corresponding either to a negative selection method or a positive selection method. For example, in accordance with the negative selection method, mature cells are removed using immunological techniques, e.g., labelling non-progenitor, non-stem cells with a panel of mouse anti-human monoclonal antibodies, then removing the mouse antibody-coated cells by adherence to rabbit-anti-mouse Ig-coated plastic dishes. See e.g., *Emerson et al, J. Clin. Invest.* (1985) 76:1286–1290. Via such procedures, stem cells and progenitor cells may be concentrated to any degree desired.

The present invention relies on a fundamental alteration of the conditions of liquid human bone marrow cultures under any of the above conditions; rapid replacement of the nutrient medium. Standard culture schedules call for medium and serum to be exchanged weekly, either as a single exchange performed weekly or a one-half medium and serum exchange performed twice weekly. In accordance with the present invention, the nutrient medium of the culture is replaced, preferably perfused, either continuously or periodically, at a rate of about 1 ml per ml of culture per about 24 to about 48 hour period, for cells cultured at a density of from $2 \times 10^6$ to $1 \times 10^7$ cells per ml. For cell densities of from $1 \times 10^4$ to $2 \times 10^6$ cells per ml the same medium exchange rate may be used. For cell densities higher than $10^7$ cells, per ml, the medium exchange rate may be increased proportionality to achieve a constant medium and serum flux per cell per unit time.

Replacement of the nutrient medium in accordance with the invention may be carried out in any manner which will achieve the result of replacing the medium, e.g., by removing an aliquot of spent culture medium and replacing it with a fresh aliquot. The flow of the aliquot being added may be by gravity, by pump, or by any other suitable means. The flow may be in any direction or multiplicity of directions, depending upon the configuration and packing of the culture. Preferably, the new medium is added to the culture in a manner such that it contacts the cell mass. Most preferably, it is added the culture in a manner mimicking in vivo perfusion, i.e., it is perfused through at least part of the cell mass and up to the whole cell mass.

Another, optional but important, embodiment of the present invention, resides in the addition of hematopoietic growth factors to the rapidly exchanged cultures. In a particularly preferred aspect of this embodiment, the cytokines IL-3 and GM-CSF are both added, together, to the medium at a rate of from 0.1 to 100 ng/ml/day, preferably about 0.5 to 10 ng/ml/day, most preferably 1 to 2 ng/ml/day. Epo may be added to the nutrient medium in an amount of from 0.001 to 10 U/ml/day, preferably 0.05 to 0.15 U/ml/day. Mast cell growth factor (MGCF, c-kit ligand, Steel factor), may be added to the medium in an amount of from 1 to 100 ng/ml/day, preferably 10 to 50 ng/ml/day. IL-1 ($\alpha$ or $\beta$) may also be added in an amount of from 10 to 100 units/ml per 3 to 5 day period. Additionally, IL-6, G-CSF, basic fibroblast growth factor, IL-7, IL-8, IL-9, IL-10, IL-11, PDGF, or EGF to be added, at a rate of from 1 to 100 ng/ml/day.

The inventors have discovered that when IL-3, GM-CSF and Epo are used as described above one obtains lineage specific development of red blood cells. Alternatively, when IL-3 and GM-CSF, with or without IL-6 or G-CSF, are used, the culture preferentially produce granulocytes. The inventors also observed that with the cultures of the invention T and B lymphocytes are lost over time.

The metabolic product level in the medium is normally maintained within a particular range. Glucose concentration is usually maintained in the range of about 5 to 20 mM. Lactate concentration is usually maintained below 35 mM. Glutamine concentration is generally maintained in the range of from about 1 to 3 mM. Ammonium concentration is usually maintained below about 2.4 mM. These concentrations can be monitored by either periodic or on line continuous measurements using known methods. See, e.g., *Caldwell et al, J. Cell Physiol.* (1991) 147:344–353.

The cells which may be cultured in accordance with the present invention may be human peripheral blood mononuclear cells, human bone marrow cells, human fetal liver cells, and/or human cord blood cells. Each of these cell masses contains human stem cells and human hematopoietic progenitor cells.

In a preferred embodiment of the invention, the cell culture may be enriched to augment the human stem cell content of the cell mass. Such enrichment may be achieved as described above, and, when used in accordance with the invention, provides the first useful means for genetic therapy via gene transfer into human bone marrow stem cells. In this embodiment, a packing cell line infected with a retrovirus, or a supernatant obtained from such a packaging cell line culture, is added to human stem cells cultured in accordance with of the invention to obtain transformed human bone marrow stem cells. The present invention provides increased levels of stem cell and human hematopoietic progenitor cell replication, whereas, by contrast, prior cultures provided only for human hematopoietic progenitor cell replication at a decreasing rate (i.e., decaying cultures). The present culture system provides, for the first time, expansion of cells in culture, which is required for retroviral infection of cells. Earlier systems in which retroviral infection was carried out on decaying cultures provided no infection of earlier cells. The present invention, particularly when it is practiced together with an enriched stem cell pool, and even more particularly when it is practiced still further with the use of hematopoietic growth factors, provides a very effective means for obtaining stem cell infection in vitro.

In accordance with the present invention one obtains cultures in which human hematopoietic progenitor cells are produced by division and differentiation from human stem cells throughout a culture period of at least five months. That is, one obtains a culture which supports stem cell survival and proliferation in culture.

Data obtained by the inventors indicates that medium perfusion rate is a very significant variable in determining the behavior of ex vivo human bone marrow cultures. This data showed that when the medium exchange rate was increased from the traditional once per week Dexter rate to a daily medium exchange rate of 7 volumes per week, a significant effect on ex vivo hematopoiesis is obtained. In experiments carried out by the inventors, all cultures displayed a significant loss of cells during the first 3 to 4 weeks. Following this decay, the cultures stabilized and the effect of a medium perfusion rate became more pronounced.

A 3.5 per week medium exchange rate led to the most prolific cultures and also to cultures of greatest longevity in terms of progenitor cell production. Of particular note, during weeks 4 to 10, the biweekly number of nonadherent cells produced was actually stable or increasing.

Over the entire course of the cultures, the cumulative number of cells produced after week 3.5 was almost threefold greater than that which is produced under the traditional Dexter culture protocol. Further, stable production of progenitor cells is maintained until week 18.

Bone marrow stomal cells may or may not be present in the cultures of the invention. In typical cultures, stromal cells are present in the cell culture in an amount of approximately $10^{-3}$ to $10^{-1}$ (stromal cells/total cells).

In another aspect of the invention, the inventors discovered that the cultures of the invention surprisingly provide increased metabolism and GM-CSF and IL-6 secretion from human bone marrow stromal cells. Whereas no GM-CSF is detected in human bone marrow stromal cells supernatant, rapid medium exchange in accordance with the invention stimulates human bone marrow stromal cells to secrete 300 centograms/ml/day to 200 picograms/ml/day of GM-CSF. Secretion of IL-6 by human bone marrow stromal cells is also increased by rapid medium exchange in accordance with the invention from 1 to 2 ng/ml/day to 2 to 4 ng/ml/day. This increase is observed both when only the rapid medium exchange rate of the invention is used, and when the rapid exchange rate together with the addition of hematopoietic growth factors is used. On the basis of data obtained by the inventors, the effect of the rapid medium exchange rates of the invention on human stromal cell production of cytokines should be observed with human stromal cells in any complex tissue culture system.

Illustratively, the medium used in accordance with the invention may comprise three basic components. The first component is a media component comprised of IMDM, MEM, DMEM, RPMI 1640, Alpha Medium or McCoy's Medium, or an equivalent known culture medium component. The second is a serum component which comprises at least horse serum or human serum and may optionally further comprise fetal calf serum, newborn calf serum, and/or calf serum. The third component is a corticosteroid, such as hydrocortisone, cortisone, dexamethasome, solumedrol, or a combination of these, preferably hydrocortisone.

The compositional make up of various media which can be used are set forth below.

| Iscove's Modified Dulbecco's Media (IMDM)[1,2,3] | | |
|---|---|---|
| COMPONENT | 380-2440 1X Liquid mg/L | 430-2280 Powder mg/L |
| INORGANIC SALTS: | | |
| CaCl$_2$ (anhyd.) | 165.00 | 165.00 |
| KCl | 330.00 | 330.00 |
| KNO$_3$ | 0.076 | 0.076 |
| MgSO$_4$ (anhyd.) | 97.67 | 97.67 |
| NaCl | 4505.00 | 4505.00 |
| NaHCO$_3$ | 3024.00 | — |
| NaH$_2$PO$_4$.H$_2$O* | 125.00 | 125.00 |
| Na$_2$SeO$_3$5H$_2$O | 0.0173 | 0.0173 |
| OTHER COMPONENTS: | | |
| D-Glucose | 4500.00 | 4500.00 |
| Phenol red | 15.00 | 15.00 |
| HEPES | 5958.00 | 5958.00 |
| Sodium pyruvate | 110.00 | 110.00 |
| AMINO ACIDS: | | |
| L-Alanine | 25.00 | 25.00 |
| L-Asparagine.H$_2$O | 28.40 | 28.40 |
| L-Arginine.HCl | 84.00 | 84.00 |
| L-Aspartic acid | 30.00 | 30.00 |
| L-Cystine.2HCl | 91.24 | 91.24 |
| L-Glutamic acid | 75.00 | 75.00 |
| L-Glutamine | 584.00 | 584.00 |
| Glycine | 30.00 | 30.00 |
| L-Histidine.HCl.H$_2$O | 42.00 | 42.00 |
| L-Isoleucine | 105.00 | 105.00 |
| L-Leucine | 105.00 | 105.00 |
| L-Lysine.HCl | 146.00 | 146.00 |
| L-Methionine | 30.00 | 30.00 |
| L-Phenylalanine | 66.00 | 66.00 |
| L-Proline | 40.00 | 40.00 |
| L-Serine | 42.00 | 42.00 |
| L-Threonine | 95.00 | 95.00 |
| L-Tryptophan | 16.00 | 16.00 |
| L-Tyrosine.2Na.2H$_2$O | 103.79 | 103.79 |
| L-Valine | 94.00 | 94.00 |
| VITAMINS: | | |
| Biotin | 0.013 | 0.013 |
| D.Ca pantothenate | 4.00 | 4.00 |
| Choline chloride | 4.00 | 4.00 |
| Folic acid | 4.00 | 4.00 |
| i-Inositol | 7.20 | 7.20 |
| Niacinamide | 4.00 | 4.00 |
| Pyridoxal.HCl | 4.00 | 4.00 |
| Riboflavin | 0.40 | 0.40 |
| Thiamine.HCl | 4.00 | 4.00 |
| Vitamin B$_{12}$ | 0.013 | 0.013 |

[1] Dulbecco, R. andFreeman, G. (1959) Virology 8,346,Smith, J. D., Freeman, G., Vogt, M., and Dulbecco, R. (1960) Virology 12, 185, Tissue Culture Standards Committee, In Vitro (1971) 6:2, 93.
[2] Iscove, N. N. and Melchers, F., J. Experimental Medicine 147, 923.
*Values shown are in conformance with Tissue Culture Standards Committee, In Vitro (1970) 9:6.;
[3] Iscove, N. N., personal communication.

| COMPONENT | 320-1885 1X Liquid mg/L | 380-2320 1X Liquid mg/L | 430-1600 Powder mg/L | 320-1965 1X Liquid mg/L | 380-2430 1X Liquid mg/L | 430-2100 Powder mg/L | 430-2800 Powder mg/L | 430-3000 Powder mg/L | 320-1960 1X Liquid mg/L | 320-1970 1X Liquid mg/L | 320-1995 1X Liquid mg/L | 430-3700 Powder mg/L | 320-1968 1X Liquid mg/L | 430-3000 Powder mg/L |
|---|---|---|---|---|---|---|---|---|---|---|---|---|---|---|
| INORGANIC SALTS: | | | | | | | | | | | | | | |
| CaCl₂ (anhyd.) | 200.00 | 200.00 | 200.00 | 200.00 | 200.00 | 200.00 | 200.00 | 200.00 | 200.00 | 200.00 | 200.00 | 200.00 | 200.00 | 200.00 |
| Fe(NO₃)₃·9H₂O | 0.10 | 0.10 | 0.10 | 0.10 | 0.10 | 0.10 | 0.10 | 0.10 | 0.10 | 0.10 | 0.10 | 0.10 | 0.10 | 0.10 |
| KCl | 400.00 | 400.00 | 400.00 | 400.00 | 400.00 | 400.00 | 400.00 | 400.00 | 400.00 | 400.00 | 400.00 | 400.00 | 400.00 | 400.00 |
| MgSO₄ (anhyd.) | — | — | 97.67 | — | — | 97.67 | 97.67 | 97.67 | — | — | — | 97.67 | — | 97.67 |
| MgSO₄·7H₂O | 200.00 | 200.00 | — | 200.00 | 200.00 | — | — | — | 200.00 | 200.00 | 200.00 | — | 200.00 | — |
| NaCl | 6400.00 | 4750.00 | 6400.00 | 6400.00 | 4750.00 | 6400.00 | 6400.00 | 6400.00 | 6400.00 | 6400.00 | 6400.00 | 4750.00 | 6400.00 | 6400.00 |
| NaHCO₃ | 3700.00 | 3700.00 | — | 3700.00 | 3700.00 | — | — | — | 3700.00 | 3700.00 | 3700.00 | — | 3700.00 | — |
| NaH₂PO₄·H₂O | 125.00 | 125.00 | 125.00 | 125.00 | 125.00 | 125.00 | 125.00 | 125.00 | 125.00 | 125.00 | 125.00 | 125.00 | 125.00 | 125.00 |
| OTHER COMPONENTS: | | | | | | | | | | | | | | |
| D-Glucose | 1000.00 | 1000.00 | 1000.00 | 4500.00 | 4500.00 | 4500.00 | 4500.00 | 4500.00 | 4500.00 | 4500.00 | 4500.00 | 4500.00 | 4500.00 | — |
| Phenol red | 15.00 | 15.00 | 15.00 | 15.00 | 15.00 | 15.00 | 15.00 | 15.00 | 15.00 | — | 15.00 | 15.00 | 15.00 | — |
| HEPES | 110.00 | 5958.00 | 110.00 | — | 5958.00 | — | 110.00 | — | — | — | 110.00 | 5958.00 | — | — |
| Sodium pyruvate | — | 110.00 | — | — | — | — | — | — | — | — | — | — | — | — |
| AMINO ACIDS: | | | | | | | | | | | | | | |
| L-Arginine·HCl | 84.00 | 84.00 | 84.00 | 84.00 | 84.00 | 84.00 | 84.00 | 84.00 | 84.00 | 84.00 | 84.00 | 84.00 | 84.00 | 84.00 |
| L-Cystine | 48.00 | 48.00 | — | 48.00 | 48.00 | — | — | — | 48.00 | 48.00 | 48.00 | — | 48.00 | — |
| L-Cystine·2HCl | — | — | 62.57 | — | — | 62.57 | 62.57 | 62.57 | — | — | — | 62.57 | — | 62.57 |
| L-Glutamine | 584.00 | 584.00 | 584.00 | 584.00 | 584.00 | 584.00 | 584.00 | 584.00 | — | — | 584.00 | 584.00 | 584.00 | — |
| Glycine | 30.00 | 30.00 | 30.00 | 30.00 | 30.00 | 30.00 | 30.00 | 30.00 | 30.00 | 30.00 | 30.00 | 30.00 | 30.00 | 30.00 |
| L-Histidine·HCl·H₂O | 42.00 | 42.00 | 42.00 | 42.00 | 42.00 | 42.00 | 42.00 | 42.00 | 42.00 | 42.00 | 42.00 | 42.00 | 42.00 | 42.00 |
| L-Isoleucine | 105.00 | 105.00 | 105.00 | 105.00 | 105.00 | 105.00 | 105.00 | 105.00 | 105.00 | 105.00 | 105.00 | 105.00 | 105.00 | 105.00 |
| L-Leucine | 105.00 | 105.00 | 105.00 | 105.00 | 105.00 | 105.00 | 105.00 | 105.00 | 105.00 | 105.00 | 105.00 | 105.00 | 105.00 | 105.00 |
| L-Lysine·HCl | 146.00 | 146.00 | 146.00 | 146.00 | 146.00 | 146.00 | 146.00 | 146.00 | 146.00 | 146.00 | 146.00 | 146.00 | 146.00 | 146.00 |
| L-Methionine | 30.00 | 30.00 | 30.00 | 30.00 | 30.00 | 30.00 | 30.00 | 30.00 | 30.00 | — | 30.00 | 30.00 | 30.00 | 30.00 |
| L-Phenylalanine | 66.00 | 66.00 | 66.00 | 66.00 | 66.00 | 66.00 | 66.00 | 66.00 | 66.00 | 66.00 | 66.00 | 66.00 | 66.00 | 66.00 |
| L-Serine | 42.00 | 42.00 | 42.00 | 42.00 | 42.00 | 42.00 | 42.00 | 42.00 | 42.00 | 42.00 | 42.00 | 42.00 | 42.00 | 42.00 |
| L-Threonine | 95.00 | 95.00 | 95.00 | 95.00 | 95.00 | 95.00 | 95.00 | 95.00 | 95.00 | 95.00 | 95.00 | 95.00 | 95.00 | 95.00 |
| L-Tryptophan | 16.00 | 16.00 | 16.00 | 16.00 | 16.00 | 16.00 | 16.00 | 16.00 | 16.00 | 16.00 | 16.00 | 16.00 | 16.00 | 16.00 |
| L-Tyrosine | 72.00 | 72.00 | — | 72.00 | 72.00 | — | — | — | 72.00 | 72.00 | 72.00 | — | 72.00 | — |
| L-Tyrosine·2Na·2H₂O | — | — | 103.79 | — | — | 103.79 | 103.79 | 103.79 | — | — | — | 103.79 | — | 103.79 |
| L-Valine | 94.00 | 94.00 | 94.00 | 94.00 | 94.00 | 94.00 | 94.00 | 94.00 | 94.00 | 94.00 | 94.00 | 94.00 | 94.00 | 94.00 |
| VITAMINS: | | | | | | | | | | | | | | |
| D·Ca pantothenate | 4.00 | 4.00 | 4.00 | 4.00 | 4.00 | 4.00 | 4.00 | 4.00 | 4.00 | 4.00 | 4.00 | 4.00 | 4.00 | 4.00 |
| Choline chloride | 4.00 | 4.00 | 4.00 | 4.00 | 4.00 | 4.00 | 4.00 | 4.00 | 4.00 | 4.00 | 4.00 | 4.00 | 4.00 | 4.00 |
| Folic acid | 4.00 | 4.00 | 4.00 | 4.00 | 4.00 | 4.00 | 4.00 | 4.00 | 4.00 | 4.00 | 4.00 | 4.00 | 4.00 | 4.00 |
| i-Inositol | 7.20 | 7.20 | 7.20 | 7.20 | 7.20 | 7.20 | 7.20 | 7.20 | 7.20 | 7.20 | 7.20 | 7.20 | — | 7.20 |
| Niacinamide | 4.00 | 4.00 | 4.00 | 4.00 | 4.00 | 4.00 | 4.00 | 4.00 | 4.00 | 4.00 | 4.00 | 4.00 | 4.00 | 4.00 |
| Pyridoxal·HCl | 4.00 | 4.00 | 4.00 | 4.00 | 4.00 | 4.00 | 4.00 | 4.00 | 4.00 | 4.00 | 4.00 | 4.00 | 4.00 | 4.00 |

-continued

| COMPONENT | 320-1885 1X Liquid mg/L | 380-2320 1X Liquid mg/L | 430-1600 Powder mg/L | 320-1965 1X Liquid mg/L | Dulbecco's[1] Modified Eagle Media (D-MEM) | | | | 320-1960 1X Liquid mg/L | 320-1970 1X Liquid mg/L | 320-1995 1X Liquid mg/L | 430-3700 Powder mg/L | 320-1968 1X Liquid mg/L | 430-3000 Powder mg/L |
|---|---|---|---|---|---|---|---|---|---|---|---|---|---|---|
| | | | | | 380-2430 1X Liquid mg/L | 430-2100 Powder mg/L | 430-2800 Powder mg/L | 430-3000 Powder mg/L | | | | | | |
| Riboflavin | 0.40 | 0.40 | 0.40 | 0.40 | 0.40 | 0.40 | 0.40 | 0.40 | 0.40 | 0.40 | 0.40 | 0.40 | 0.40 | 0.40 |
| Thiamine.HCl | 4.00 | 4.00 | 4.00 | 4.00 | 4.00 | 4.00 | 4.00 | 4.00 | 4.00 | 4.00 | 4.00 | 4.00 | 4.00 | 4.00 |

[1]Dulbecco, R. and Freeman, G. (1959) Virology 8, 396. Smith, J. D., Freeman, G., Vogt, M. and Dulbecco, R. (1960) Virology 12, 185. Tissue Culture Standards Committee, In Vitro 6:2, 93.
[a]Values shown are in conformance with the Tissue Culture Standards Committee, In Vitro (1970) 9:6.

Minimum Essential Media (MEM)[1]

| COMPONENT | 320-2561[2] 1X Liquid mg/L | 410-2000[2] Powder mg/L | 320-2571[2] 1X Liquid mg/L | 410-1900[2] Powder mg/L | 320-2570 1X Liquid mg/L | 320-1090 1X Liquid mg/L | 380-2360 1X Liquid mg/L | 330-1430 1X Liquid mg/L | 410-1700 Powder mg/L | 320-1890 1X Liquid mg/L | 320-1096 1X Liquid mg/L | 410-2400 Powder mg/L | 320-1097 1X Liquid mg/L | 410-2500 Powder mg/L |
|---|---|---|---|---|---|---|---|---|---|---|---|---|---|---|
| INORGANIC SALTS: | | | | | | | | | | | | | | |
| CaCl$_2$ (anhyd.) | 200.00 | 200.00 | 200.00 | 200.00 | 200.00 | 200.00 | 200.00 | 200.00 | 200.00 | 200.00 | 200.00 | 200.00 | 200.00 | 200.00 |
| KCl | 400.00 | 400.00 | 400.00 | 400.00 | 400.00 | 400.00 | 400.00 | 400.00 | 400.00 | 400.00 | 400.00 | 400.00 | 400.00 | 400.00 |
| MgSO$_4$ (anhyd.) | — | 97.67 | — | 97.67 | — | — | — | — | 97.67 | — | — | 97.67 | — | 97.67 |
| MgSO$_4$.7H$_2$O | 200.00 | — | 200.00 | — | 200.00 | 200.00 | 200.00 | 200.00 | — | 200.00 | 200.00 | — | 200.00 | — |
| NaCl | 6800.00 | 6800.00 | 6800.00 | 6800.00 | 6800.00 | 6800.00 | 6350.00 | 6800.00 | 6800.00 | 6800.00 | 6800.00 | 6800.00 | 6800.00 | 6800.00 |
| NaHCO$_3$ | 2200.00 | — | 2200.00 | — | 2200.00 | 2200.00 | 2200.00 | — | — | 2200.00 | 1500.00 | — | 2200.00 | — |
| NaH$_2$PO$_4$.H$_2$O[a] | 140.00 | 140.00 | 140.00 | 140.00 | 140.00 | 140.00 | 140.00 | 140.00 | 140.00 | 140.00 | 140.00 | 140.00 | — | — |
| OTHER COMPONENTS | | | | | | | | | | | | | | |
| D-Glucose | 1000.00 | 1000.00 | 1000.00 | 1000.00 | 1000.00 | 1000.00 | 1000.00 | 1000.00 | 1000.00 | 1000.00 | 1000.00 | 1000.00 | 1000.00 | 1000.00 |
| HEPES | — | — | — | — | — | — | 5958.00 | — | — | — | — | — | — | — |
| Lipoic acid | 0.20 | 0.20 | 0.20 | 0.20 | — | — | — | — | — | — | — | — | — | — |
| Phenol red | 10.00 | 10.00 | 10.00 | 10.00 | 10.00 | 10.00 | 10.00 | 100.00 | 6.00 | 10.00 | 10.00 | 10.00 | 10.00 | 10.00 |
| Sodium pyruvate | 110.00 | 110.00 | 110.00 | 110.00 | — | — | — | — | 100.00 | — | — | — | — | — |
| Sodium succinate | — | — | — | — | — | — | — | — | 75.00 | — | — | — | — | — |
| Succinic acid | — | — | — | — | — | — | — | — | — | — | — | — | — | — |
| AMINO ACIDS: | | | | | | | | | | | | | | |
| L-Alanine | 25.00 | 25.00 | 25.00 | 25.00 | — | — | — | — | — | — | — | — | — | — |
| L-Arginine | 105.00 | — | 105.00 | — | — | — | — | — | — | — | — | — | — | — |
| L-Arginine.HCl | — | 126.64 | — | 126.64 | 126.00 | 126.00 | 126.00 | 1260.00 | 126.00 | 126.00 | 126.00 | 126.00 | 126.00 | 126.00 |
| L-Asparagine.H$_2$O | 50.00 | 50.00 | 50.00 | 50.00 | — | — | — | — | — | — | — | — | — | — |
| L-Aspartic acid | 30.00 | 30.00 | 30.00 | 30.00 | — | — | — | — | — | — | — | — | — | — |
| L-Cystine | 24.00 | — | 24.00 | — | 24.00 | 24.00 | 24.00 | 240.00 | — | 24.00 | — | — | 24.00 | — |
| L-Cystine.2HCl | — | 31.28 | — | 31.28 | — | — | — | — | 31.00 | — | 31.00 | 31.29 | — | 31.29 |
| L-Cystine.HCl.H$_2$O | 100.00 | 100.00 | 100.00 | 100.00 | — | — | — | — | — | — | — | — | — | — |
| L-Glutamic acid | 75.00 | 75.00 | 75.00 | 75.00 | — | — | — | — | — | — | — | — | — | — |
| L-Glutamine | 292.00 | 292.00 | 292.00 | 292.00 | 292.00 | — | — | — | — | — | — | 292.00 | 292.00 | 292.00 |
| Glycine | 50.00 | 50.00 | 50.00 | 50.00 | — | — | — | — | — | — | — | — | — | — |
| L-Histidine | 31.00 | 50.00 | 31.00 | 50.00 | — | — | — | — | — | — | — | — | — | — |
| L-Histidine.HCl.H$_2$O | — | 42.00 | — | 42.00 | 42.00 | 42.00 | 42.00 | 420.00 | 42.00 | 42.00 | 42.00 | 42.00 | 42.00 | 42.00 |
| L-Isoleucine | 52.40 | 52.40 | 52.40 | 52.40 | 52.00 | 52.00 | 52.00 | 520.00 | 52.00 | 52.00 | 52.00 | 52.00 | 52.00 | 52.00 |
| L-Leucine | 52.40 | 52.40 | 52.40 | 52.40 | 52.00 | 52.00 | 52.00 | 520.00 | 52.00 | — | 52.00 | — | 52.00 | 52.00 |
| L-Lysine | 58.00 | — | 58.00 | — | — | — | — | — | — | — | — | — | — | — |
| L-Lysine.HCl | — | 72.50 | — | 72.50 | 72.50 | 72.50 | 72.50 | 725.00 | 72.50 | 72.50 | 72.50 | 72.50 | 72.50 | 72.50 |
| L-Methionine | 15.00 | 15.00 | 15.00 | 15.00 | 15.00 | 15.00 | 15.00 | 150.00 | 15.00 | 15.00 | 15.00 | 15.00 | 15.00 | 15.00 |
| L-Phenylalanine | 32.00 | 32.00 | 32.00 | 32.00 | 32.00 | 32.00 | 32.00 | 320.00 | 32.00 | 32.00 | 32.00 | 32.00 | 32.00 | 32.00 |
| L-Proline | 40.00 | 40.00 | 40.00 | 40.00 | — | — | — | — | — | — | — | — | — | — |
| L-Serine | 25.00 | 25.00 | 25.00 | 25.00 | — | — | — | — | — | — | — | — | — | — |
| L-Threonine | 48.00 | 48.00 | 48.00 | 48.00 | 48.00 | 48.00 | 48.00 | 480.00 | 48.00 | 48.00 | 48.00 | 48.00 | 48.00 | 48.00 |
| L-Tryptophan | 10.00 | 10.00 | 10.00 | 10.00 | 10.00 | 10.00 | 10.00 | 100.00 | 10.00 | 10.00 | 10.00 | 10.00 | 10.00 | 10.00 |
| L-Tyrosine | 36.00 | — | 36.00 | — | 36.00 | 36.00 | 36.00 | 360.00 | 36.00 | 36.00 | — | — | 36.00 | — |
| L-Tyrosine.2Na.2H$_2$O | — | 51.90 | — | 51.90 | — | — | — | — | — | — | 51.90 | 51.90 | — | 51.90 |
| D-Valine | — | — | — | — | 92.00 | — | — | — | — | — | — | — | — | — |

-continued

| | Minimum Essential Media (MEM)[1] | | | | | | | | | | | | | |
|---|---|---|---|---|---|---|---|---|---|---|---|---|---|---|
| COMPONENT | 320-2561[2] 1X Liquid mg/L | 410-2000[2] Powder mg/L | 320-2571[2] 1X Liquid mg/L | 410-1900[2] Powder mg/L | 320-2570 1X Liquid mg/L | 320-1090 1X Liquid mg/L | 380-2360 1X Liquid mg/L | 330-1430 1X Liquid mg/L | 410-1700 Powder mg/L | 320-1890 1X Liquid mg/L | 320-1096 1X Liquid mg/L | 410-2400 Powder mg/L | 320-1097 1X Liquid mg/L | 410-2500 Powder mg/L |
| L-Valine | 46.00 | 46.00 | 46.00 | 46.00 | — | 46.00 | 46.00 | 460.00 | 46.00 | 46.00 | 46.00 | 46.00 | 46.00 | 46.00 |
| VITAMINS: | | | | | | | | | | | | | | |
| L-Ascorbic acid | 50.00 | 50.00 | 50.00 | 50.00 | — | — | — | — | — | — | — | — | — | — |
| Biotin | 0.10 | 0.10 | 0.10 | 0.10 | — | — | — | — | — | — | — | — | — | — |
| D-Ca pantothenate | 1.00 | 1.00 | 1.00 | 1.00 | 1.00 | 1.00 | 1.00 | 10.00 | 1.00 | 1.00 | 1.00 | 1.00 | 1.00 | 1.00 |
| Choline bitartrate | — | — | — | — | — | — | — | — | — | — | — | — | — | — |
| Choline chloride | 1.00 | 1.00 | 1.00 | 1.00 | 1.00 | 1.00 | 1.00 | 10.00 | 1.00 | 1.00 | 1.00 | 1.00 | 1.00 | 1.00 |
| Folic acid | 1.00 | 1.00 | 1.00 | 1.00 | 1.00 | 1.00 | 1.00 | 10.00 | 1.00 | 1.00 | 1.00 | 1.00 | 1.00 | 1.00 |
| i-Inositol | 2.00 | 2.00 | 2.00 | 2.00 | 2.00 | 2.00 | 2.00 | 20.00 | 1.80 | 2.00 | 2.00 | 2.00 | 2.00 | 2.00 |
| Niacinamide | 1.00 | 1.00 | 1.00 | 1.00 | 1.00 | 1.00 | 1.00 | 10.00 | 1.00 | 1.00 | 1.00 | 1.00 | 1.00 | 1.00 |
| Pyridoxal.HCl | 1.00 | 1.00 | 1.00 | 1.00 | 1.00 | 1.00 | 1.00 | 10.00 | 1.00 | 1.00 | 1.00 | 1.00 | 1.00 | 1.00 |
| Riboflavin | 0.10 | 0.10 | 0.10 | 0.10 | 0.10 | 0.10 | 0.10 | 1.00 | 0.10 | 0.10 | 0.10 | 0.10 | 0.10 | 0.10 |
| Thiamine.HCl | 1.00 | 1.00 | 1.00 | 1.00 | 1.00 | 1.00 | 1.00 | 10.00 | 1.00 | 1.00 | 1.00 | 1.00 | 1.00 | 1.00 |
| Vitamin B$_{12}$ | 1.36 | 1.36 | 1.36 | 1.36 | — | — | — | — | — | — | — | — | — | — |
| RIBONUCLEOSIDES: | | | | | | | | | | | | | | |
| Adenosine | — | — | 10.00 | 10.00 | — | — | — | — | — | — | — | — | — | — |
| Cyodine | — | — | 10.00 | 10.00 | — | — | — | — | — | — | — | — | — | — |
| Guanosine | — | — | 10.00 | 10.00 | — | — | — | — | — | — | — | — | — | — |
| Uridine | — | — | 10.00 | 10.00 | — | — | — | — | — | — | — | — | — | — |
| DEOXYRIBONUCLEOSIDES: | | | | | | | | | | | | | | |
| 2'Deoxyadenosine | — | — | 10.00 | 10.00 | — | — | — | — | — | — | — | — | — | — |
| 2'Deoxycyodine.HCl | — | — | 11.00 | 11.00 | — | — | — | — | — | — | — | — | — | — |
| 2'Deoxyguanosine | — | — | 10.00 | 10.00 | — | — | — | — | — | — | — | — | — | — |
| Thymidine | — | — | 10.00 | 10.00 | — | — | — | — | — | — | — | — | — | — |

[1]Eagle, H. (1959) Science. 130, 432.
[2]Nature, New Biology (1971) 230, 310.
*Original formula lists this component as NaH$_2$PO$_4$.2H$_2$O.

RPMI Media 1640[1]

| COMPONENT | 320-1870 1X Liquid mg/L | 320-1875 1X Liquid mg/L | 330-2511 1X Liquid mg/L | 380-2400 1X Liquid mg/L | 430-1800 Powder mg/L | 430-3200 Powder mg/L | 430-3400 Powder mg/L | 320-1835 1X Liquid mg/L | 320-12877 1X Liquid mg/L |
|---|---|---|---|---|---|---|---|---|---|
| INORGANIC SALTS: | | | | | | | | | |
| Ca(NO$_3$)$_2$.4H$_2$O | 100.00 | 100.00 | 1000.00 | 100.00 | 100.00 | 100.00 | 100.00 | 100.00 | 100.00 |
| KCl | 400.00 | 400.00 | 4000.00 | 400.00 | 400.00 | 400.00 | 400.00 | 400.00 | 400.00 |
| MgSO$_4$ (anhyd.) | — | — | — | — | 48.84 | 48.84 | 48.84 | — | — |
| MgSO$_4$.7H$_2$O | 100.00 | 100.00 | 1000.00 | 100.00 | — | — | — | 100.00 | 100.00 |
| NaCl | 6000.00 | 6000.00 | 60000.00 | 5300.00 | 6000.00 | 6000.00 | 5850.00 | 6000.00 | 6000.00 |
| NaHCO$_3$ | 2000.00 | 2000.00 | — | 2000.00 | — | — | — | 2000.00 | 2000.00 |
| Na$_2$HPO$_4$ (anhyd.) | — | — | — | — | 800.00 | 800.00 | 800.00 | — | — |
| NaH$_2$PO$_4$.H$_2$O | 1512.00 | 1512.00 | 15120.00 | 1512.00 | — | — | — | 1512.00 | — |
| OTHER COMPONENTS: | | | | | | | | | |
| D-Glucose | 2000.00 | 2000.00 | 20000.00 | 2000.00 | 2000.00 | 2000.00 | 2000.00 | 2000.00 | 2000.00 |
| Glutathione (reduced) | 1.00 | 1.00 | 1.00 | 1.00 | 1.00 | 1.00 | 1.00 | 1.00 | 1.00 |
| HEPES | — | — | — | 5958.00 | — | — | 5957.50 | — | — |
| Phenol red | 5.00 | 5.00 | 5.00 | 5.00 | 5.00 | — | 5.00 | — | 5.00 |
| AMINO ACIDS: | | | | | | | | | |
| L-Arginine | 200.00 | 200.00 | 2000.00 | 200.00 | 200.00 | 200.00 | 200.00 | 200.00 | 200.00 |
| L-Asparagine | 50.00 | 50.00 | 500.00 | 50.00 | 50.00 | 50.00 | 50.00 | 50.00 | 50.00 |
| L-Aspartic acid | 20.00 | 20.00 | 200.00 | 20.00 | 20.00 | 20.00 | 20.00 | 20.00 | 20.00 |
| L-Cystine | 50.00 | 50.00 | 500.00 | 50.00 | — | — | — | 50.00 | 50.00 |
| L-Cystine.2HCl | — | — | — | — | 65.15 | 65.15 | 65.15 | — | — |
| L-Glutamic acid | 20.00 | 20.00 | 200.00 | 20.00 | 20.00 | 20.00 | 20.00 | 20.00 | 20.00 |
| L-Glutamine | — | 300.00 | 3000.00 | 300.00 | 300.00 | 300.00 | 300.00 | 300.00 | 300.00 |
| Glycine | 10.00 | 10.00 | 100.00 | 10.00 | 10.00 | 10.00 | 10.00 | 10.00 | 10.00 |
| L-Histidine | 15.00 | 15.00 | 150.00 | 15.00 | 15.00 | 15.00 | 15.00 | 15.00 | 15.00 |
| L-Hydroxypyroline | 20.00 | 20.00 | 200.00 | 20.00 | 20.00 | 20.00 | 20.00 | 20.00 | 20.00 |
| L-Isoleucine | 50.00 | 50.00 | 500.00 | 50.00 | 50.00 | 50.00 | 50.00 | 50.00 | 50.00 |
| L-Leucine | 50.00 | 50.00 | 500.00 | 50.00 | 50.00 | 50.00 | 50.00 | 50.00 | 50.00 |
| L-Lysine.HCl | 40.00 | 40.00 | 400.00 | 40.00 | 40.00 | 40.00 | 40.00 | 40.00 | 40.00 |
| L-Methionine | 15.00 | 15.00 | 150.00 | 15.00 | 15.00 | 15.00 | 15.00 | 15.00 | 15.00 |
| L-Phenylalanine | 15.00 | 15.00 | 150.00 | 15.00 | 15.00 | 15.00 | 15.00 | 15.00 | 15.00 |
| L-Proline | 20.00 | 20.00 | 200.00 | 20.00 | 20.00 | 20.00 | 20.00 | 20.00 | 20.00 |
| L-Serine | 30.00 | 30.00 | 300.00 | 30.00 | 30.00 | 30.00 | 30.00 | 30.00 | 30.00 |
| L-Threonine | 20.00 | 20.00 | 200.00 | 20.00 | 20.00 | 20.00 | 20.00 | 20.00 | 20.00 |
| L-Tryptophan | 5.00 | 5.00 | 50.00 | 5.00 | 5.00 | 5.00 | 5.00 | 5.00 | 5.00 |
| L-Tyrosine | 20.00 | 20.00 | 200.00 | 20.00 | — | — | — | 20.00 | 20.00 |
| L-Tyrosine.2Na.2H$_2$O | — | — | — | — | 28.83 | 28.83 | 28.83 | — | — |
| L-Valine | 20.00 | 20.00 | 200.00 | 20.00 | 20.00 | 20.00 | 20.00 | 20.00 | 20.00 |
| VITAMINS: | | | | | | | | | |
| Biotin | 0.20 | 0.20 | 2.00 | 0.20 | 0.20 | 0.20 | 0.20 | 0.20 | 0.20 |
| D.Ca pantothenate | 0.25 | 0.25 | 2.50 | 0.25 | 0.25 | 0.25 | 0.25 | 0.25 | 0.25 |
| Choline chloride | 3.00 | 3.00 | 30.00 | 3.00 | 3.00 | 3.00 | 3.00 | 3.00 | 3.00 |
| Folic acid | 1.00 | 1.00 | 10.00 | 1.00 | 1.00 | 1.00 | 1.00 | 1.00 | 1.00 |
| i-Inositol | 35.00 | 35.00 | 350.00 | 35.00 | 35.00 | 35.00 | 35.00 | 35.00 | 35.00 |
| Niacinamide | 1.00 | 1.00 | 10.00 | 1.00 | 1.00 | 1.00 | 1.00 | 1.00 | 1.00 |
| Para.aminobenzoic acid | 1.00 | 1.00 | 10.00 | 1.00 | 1.00 | 1.00 | 1.00 | 1.00 | 1.00 |
| Pyridoxine.HCl | 1.00 | 1.00 | 10.00 | 1.00 | 1.00 | 1.00 | 1.00 | 1.00 | 1.00 |
| Riboflavin | 0.20 | 0.20 | 2.00 | 0.20 | 0.20 | 0.20 | 0.20 | 0.20 | 0.20 |
| Thiamine.HCl | 1.00 | 1.00 | 10.00 | 1.00 | 1.00 | 1.00 | 1.00 | 1.00 | 1.00 |
| Vitamin B$_{12}$ | 0.005 | 0.005 | 0.05 | 0.005 | 0.005 | 0.005 | 0.005 | 0.005 | 0.005 |

[1] Moore, G. E., Gerner, R. E., and Franklin, H. A. (1967) J.A.M.A. 199,519.

McCoy's 5A Media (modified)[1,2,3]

| COMPONENT | 320-6600 1X Liquid mg/L | 380-2330 1X Liquid mg/L | 430-1500 Powder mg/L | 320-6606 1X Liquid mg/L | 320-6601[a] 1X Liquid mg/L | 320-6610 1X Liquid mg/L | 320-6620 1X Liquid mg/L | 320-6630 1X Liquid mg/L |
|---|---|---|---|---|---|---|---|---|
| INORGANIC SALTS: | | | | | | | | |
| CaCl$_2$ (anhyd.) | 100.00 | 100.00 | 100.00 | — | 140.00 | 100.00 | 100.00 | 100.00 |
| KCl | 400.00 | 400.00 | 400.00 | 400.00 | 400.00 | 400.00 | 400.00 | 400.00 |
| KH$_2$PO$_4$ | — | — | — | — | 60.00 | — | — | — |
| MgCl$_2$.6M$_2$O | — | — | — | — | 100.00 | — | — | — |
| MgSO$_4$ (anhyd.) | — | — | 97.67 | — | — | — | — | — |
| MgSO$_4$.7H$_2$O | 200.00 | 200.00 | — | 200.00 | 100.00 | 200.00 | 200.00 | 200.00 |
| NaCl | 6460.00 | 5100.00 | 6460.00 | 6460.00 | 8000.00 | 6460.00 | 6460.00 | 6460.00 |
| NaHCO$_3$ | 2200.00 | 2200.00 | — | 2200.00 | 350.00 | 2200.00 | 2200.00 | 2200.00 |

-continued

McCoy's 5A Media (modified)[1,2,3]

| COMPONENT | 320-6600 1X Liquid mg/L | 380-2330 1X Liquid mg/L | 430-1500 Powder mg/L | 320-6606 1X Liquid mg/L | 320-6601[a] 1X Liquid mg/L | 320-6610 1X Liquid mg/L | 320-6620 1X Liquid mg/L | 320-6630 1X Liquid mg/L |
|---|---|---|---|---|---|---|---|---|
| $NaH_2PO_4.H_2O$ | 580.00 | 580.00 | 580.00 | 1400.00 | — | 580.00 | 580.00 | 580.00 |
| $Na_2HPO_4.7H_2O$ | — | — | — | — | 90.00 | — | — | — |
| OTHER COMPONENTS: | | | | | | | | |
| Bacto-peptone | 600.00 | 600.00 | 600.00 | 600.00 | 600.00 | 600.00 | 600.00 | 600.00 |
| Fetal Bovine Serum | — | — | — | — | — | c | c | c |
| D-Glucose | 3000.00 | 3000.00 | 3000.00 | 3000.00 | 1000.00 | 3000.00 | 3000.00 | 3000.00 |
| Glutathione (reduced) | 0.50 | 0.50 | 0.50 | 0.50 | 0.50 | 0.50 | 0.50 | 0.50 |
| HEPES | — | 5958.00 | — | — | — | — | — | — |
| Phenol red | 10.00 | 10.00 | 10.00 | 10.00 | 10.00 | 10.00 | 10.00 | 10.00 |
| AMINO ACIDS: | | | | | | | | |
| L-Alanine | 13.90 | 13.90 | 13.90 | 13.90 | 13.90 | 13.90 | 13.90 | 13.90 |
| L-Arginine.HCl | 42.10 | 42.10 | 42.10 | 42.10 | 42.10 | 42.10 | 42.10 | 42.10 |
| L-Asparagine | 45.00 | 45.00 | 45.00 | 45.00 | 45.00 | 45.00 | 45.00 | 45.00 |
| L-Aspartic acid | 19.97 | 19.97 | 19.97 | 19.97 | 19.97 | 19.97 | 19.97 | 19.97 |
| L-Cystine° | 31.50 | 31.50 | 31.50 | 31.50 | 31.50 | 31.50 | 31.50 | 31.50 |
| L-Glutamic acid | 22.10 | 22.10 | 22.10 | 22.10 | 22.10 | 22.10 | 22.10 | 22.10 |
| L-Glutamine | 219.20 | 219.20 | 219.20 | 219.20 | 219.20 | 219.20 | 219.20 | 219.20 |
| Glycine | 7.50 | 7.50 | 7.50 | 7.50 | 7.50 | 7.50 | 7.50 | 7.50 |
| L-Histidine.HCl.$H_2O$ | 20.96 | 20.96 | 20.96 | 20.96 | 20.96 | 20.96 | 20.96 | 20.96 |
| L-Hydroxyproline | 19.70 | 19.70 | 19.70 | 19.70 | 19.70 | 19.70 | 19.70 | 19.70 |
| L-Isoleucine | 39.36 | 39.36 | 39.36 | 39.36 | 39.36 | 39.36 | 39.36 | 39.36 |
| L-Leucine | 39.36 | 39.36 | 39.36 | 39.36 | 39.36 | 39.36 | 39.36 | 39.36 |
| L-Lysine.HCl | 36.50 | 36.50 | 36.50 | 36.50 | 36.50 | 36.50 | 36.50 | 36.50 |
| L-Methionine | 14.90 | 14.90 | 14.90 | 14.90 | 14.90 | 14.90 | 14.90 | 14.90 |
| L-Phenylalanine | 16.50 | 16.50 | 16.50 | 16.50 | 16.50 | 16.50 | 16.50 | 16.50 |
| L-Proline | 17.30 | 17.30 | 17.30 | 17.30 | 17.30 | 17.30 | 17.30 | 17.30 |
| L-Serine | 26.30 | 26.30 | 26.30 | 26.30 | 26.30 | 26.30 | 26.30 | 26.30 |
| L-Threonine | 17.90 | 17.90 | 17.90 | 17.90 | 17.90 | 17.90 | 17.90 | 17.90 |
| L-Tryptophan | 3.10 | 3.10 | 3.10 | 3.10 | 3.10 | 3.10 | 3.10 | 3.10 |
| L-Tyrosine | 18.10 | 18.10 | 18.10 | 18.10 | 18.10 | 18.10 | 18.10 | 18.10 |
| L-Tyrosine.2Na.$2H_2O$ | — | — | 26.10 | — | — | — | — | — |
| L-Valine | 17.60 | 17.60 | 17.60 | 17.60 | 17.60 | 17.60 | 17.60 | 17.60 |
| VITAMINS: | | | | | | | | |
| Ascorbic acid | 0.50 | 0.50 | 0.50 | 0.50 | 0.50 | 0.50 | 0.50 | 0.50 |
| Biotin | 0.20 | 0.20 | 0.20 | 0.20 | 0.20 | 0.20 | 0.20 | 0.20 |
| Choline chloride | 5.00 | 5.00 | 5.00 | 5.00 | 5.00 | 5.00 | 5.00 | 5.00 |
| D-Ca pantothenate | 0.20 | 0.20 | 0.20 | 0.20 | 0.20 | 0.20 | 0.20 | 0.20 |
| Folic acid | 10.00 | 10.00 | 10.00 | 10.00 | 10.00 | 10.00 | 10.00 | 10.00 |
| i-Inositol | 36.00 | 36.00 | 36.00 | 36.00 | 36.00 | 36.00 | 36.00 | 36.00 |
| Niacinamide | 0.50 | 0.50 | 0.50 | 0.50 | 0.50 | 0.50 | 0.50 | 0.50 |
| Nicolinic acid | 0.50 | 0.50 | 0.50 | 0.50 | 0.50 | 0.50 | 0.50 | 0.50 |
| Para.aminobenzoic acid | 1.00 | 1.00 | 1.00 | 1.00 | 1.00 | 1.00 | 1.00 | 1.00 |
| Pyridoxal.HCl | 0.50 | 0.50 | 0.50 | 0.50 | 0.50 | 0.50 | 0.50 | 0.50 |
| Pyridoxine.HCl | 0.50 | 0.50 | 0.50 | 0.50 | 0.50 | 0.50 | 0.50 | 0.50 |
| Riboflavin | 0.20 | 0.20 | 0.20 | 0.20 | 0.20 | 0.20 | 0.20 | 0.20 |
| Thiamine.HCl | 0.20 | 0.20 | 0.20 | 0.20 | 0.20 | 0.20 | 0.20 | 0.20 |
| Vitamin $B_{12}$ | 2.00 | 2.00 | 2.00 | 2.00 | 2.00 | 2.00 | 2.00 | 2.00 |

[1]McCoy, T. A., Maxwell, M., and Kruse, P. F. (1959) Proc. Soc. Exper. Biol. Med. 100, 115.
[2]Hsu, T. C. and Kellogg, D. S., Jr. (1960) J. Nat. Cancer Inst. 25, 221.
[3]Iwakata, S. and Grace, J. T., Jr. (1964) N.Y.J. Med. 64:18, 2279.
[4]McCoy's 5A Medium formulated with Hanks' and Suspension Salts is a GIBCO modification and is not cited in references 1–3.
[a]HCl form listed by the Tissue Culture Standards Committee, In Vitro (1974) 9:0.
[b]Monohydrate form listed by the Tissue Culture Standards Committee, In Vitro (1974) 9:6.
[c]Fetal Bovine Serum Supplementation:
Cat. No. FBS 320-6610 10% v/v
320-6620 20% v/v
320-6630 30% v/v The serum component may be present in the culture in an amount of at least 1% (v/v) to 50% (v/v). The serum concentration may be preferably in the neighborhood of 15 to 30% (v/v). For higher serum concentrations, the exchange rate is increased proportionately. The third component may be present in an amount of from $10^{-7}$ M to $10^{-4}$ M, and is preferably present in an amount of from $5\times10^{-6}$ to $5\times10^{-5}$ M. The media component represents the balance such that all three components add up to 100%. Alternatively the serum component can be replaced by any of several standard serum replacement mixtures which typically include insulin, albumin, and lecithin or cholesterol. See, *Migliaccio et al, Exp. Hematol.* (1990) (18:1049–1055, *Iscove et al, Exp. cell*

Res. (1980) 126:121–126, and *Dainiak et al, J. Clin. Invest.* (1985) 76:1237–1242.

Having generally described this invention, a further understanding can be obtained by reference to certain specific examples which are provided herein for purposes of illustration only and are not intended to be limiting unless otherwise specified.

Medium Replacement

Materials and Methods:

Cells: Human bone marrow cells were obtained from heparinized aspirates from the iliac crest of informed and consenting individuals. The bone marrow was separated by a Ficoll-Paque (Pharmacia, No. 17-0840-02) density gradient centrifugation and the low density cells (<1.077 gm/cm$^3$) were collected and washed 3 times with Iscove's Modified Dulbecco's Medium (IMDM). The cells were counted between the second and third washes. The cells were then seeded onto 24-well tissue culture plates (Costar No. 3524) in duplicate or triplicate at 1, 2, and 5·10$^6$ cells/ml at 322 µl/well.

Long-term culture conditions: The low density cells were incubated in IMDM supplemented with 10% fetal calf serum (Hyclone Laboratories, 10% horse serum (Hyclone Laboratories), 1% penicillin/streptomycin (Sigma, 10,000 U/ml penicillin G and 10 mg/ml streptomycin, Cat. No. P3539), and 10$^{-5}$ M hydrocortisone (17-Hydroxycorticosterone, Sigma, Cat. No. H0888) in a humidified 5% $CO_2$/95% air atmosphere. The cultures were treated with one of three medium exchange schedules, 100% daily medium exchange (7/wk), 50% daily medium exchange (3.5/wk), or 50% biweekly medium exchange (1/wk). Twice per week during the medium exchange, 50% of the non-adherent cells were removed from each culture well and counted using a hemocytometer.

When the cells were removed for counting (twice/week), all of the medium removed during feeding of the 3.5/wk and 1/wk cultures was saved for cell counts and fresh medium returned to the wells. The 7/wk cultures required saving ½ of the removed medium for cell counts, while centrifuging and returning the non-adherent cells in the remaining ½ of the medium removed. Fresh medium was then added to each well to replace the medium removed for cell counts. On days when the cells were not removed for counting, 100% or 50% of the medium was removed from each of the 7/wk and 3.5/wk culture wells respectively, the cells were centrifuged and returned to the original wells with additional fresh medium.

Methylcellulose and morphologic assays: One every other week the non-adherent cells removed for cell counts were plated in methylcellulose in the presence of erythropoietin, GM-CSF, and IL-3, and the Granulocyte Macrophase-Colony Forming Units (CFU-GM) were enumerated. Aliquot of removed cells were cytocentrifuged, stained with Wright-Giemsa, and differential cell counts performed.

Statistical analysis: The biweekly cell production results are expressed as the mean ±SEM from replicate cultures. The probability of significant differences between groups of cultures was determined by comparing the normalized cumulative cell production values from the rapidly exchanged cultures (7/wk and 3.5/wk) to the matched control cultures (1/wk) using a paired t-test. Statistical significance was taken at the 5% level.

Results:

Kinetics of nonadherent cell production: Nonadherent cell production was examined both as a function of inoculum cell density (over the range 1–5·10$^6$ cells/ml) and medium exchange rate. The medium exchange rate was varied from one medium volume exchange per week, the traditional Dexter culture rate, to seven medium volume exchanges per week. The biweekly number of cells collected was normalized by dividing by the number of cell inoculated per culture.

At each medium exchange rate, the normalized cell collection curves did not change significantly with inoculum density. The cell production for the cultures maintained at the three medium perfusion rates of 7/wk, 3.5/wk and 1/wk were similar when normalized to the number of cells inoculated per culture. Comparison of the final cumulative cell productions between inoculum densities showed no significant differences, at any of the three medium exchange rates ($p > 0.20$ by a paired t-test for all pairs of samples).

The medium exchange rate, in contrast, strongly influenced the rate and longevity of cell production in these cultures. Cell production of the cultures exchanged at 1/wk (control), 3.5/wk, and 7/wk all decayed over the first few weeks. Differences in culture productivity, however, became apparent after week 3 in culture. Between weeks 3 to 10, the cell production was constant in the 7/wk cultures, constant at a lower level in the 1/wk cultures, but increased exponentially in the 3.5/wk cultures. After weeks 10 to 12, cell production declined in all cultures until culture termination.

Results for the 1/wk exchanged cultures are equivalent to those commonly observed in traditional human Dexter cultures in a variety of systems, whereas the rapidly exchanged cultures of 3.5 and 7/wk showed increased cell productivity when compared to previous optimum culture methods. Cultures in which ½ of the medium was exchanged daily (3.5/wk) maintained increased cell production for substantially longed than either the control (1/wk) or complete daily exchange (7/wk) cultures. Between weeks 3 and 9, the number of nonadherent cells collected from the 3.5/wk exchanged cultures increased exponentially with a doubling every 2.1 weeks.

The cell production under the 3.5/wk and 1/wk protocols can be directly compared by plotting the cell production under the 3.5/wk exchange rate as a percentage of the production of the cultures with an exchange rate of 1/wk. This comparison shows that during the initial decay phase the cell production under the two protocols is similar. However, between weeks 3.5 and 18, the cell production under the 3.5/wk exchange rate is consistently higher.

The proliferative potential of the cultures can thus be measured by their ability to produce cells following the initial decay. The normalized cumulative cell production following week 3 ($\Sigma^n_{i=7}$, $C_i/C_o$ was independent of the cell inoculation density for the medium exchange rates of 7/wk, 3.5/wk. Cell production data from the cultures at similar medium exchange rates were qualitatively and statistically similar, and were therefore density averaged and combined (bottom panel) to obtain a larger statistical sample. The density averaged cumulative cell production between weeks 3.5 and 20 was: 0.22 for the 7/wk; 0.40 for the 3.5/wk; and 0.15 for the 1/wk cultures. The increase in the medium exchange rate from 1/wk to 7/wk thus increased the cell production about 60% over the typical Dexter culture medium exchange schedule. The 3.5/wk exchange rate resulted in almost 3-fold cumulative cell production increase compared to the 1/wk Dexter protocol. Statistical analysis of these data using a paired t-test, demonstrated significant differences between both the 7/wk vs. 1/wk and the 3.5/wk vs. 1/wk at the 5% level of significance. The medium exchange rate of 3.5/wk thus improves the cell production rate over the traditional Dexter protocol of 1/wk.

Granulocyte-macrophase progenitor cell production:

Granulocyte-macrophase progenitor cell assays were performed from replicates of a given medium perfusion schedule and inoculum density (Table 1). The medium perfusion rate had a pronounced effect on the number of granulocyte-macrophage progenitor cells produced. The 3.5/wk medium exchange cultures showed the greatest longevity in terms of progenitor cell production. These cultures produced progenitors at a stable rate between weeks 4 and 18.

The optimum conditions in terms of progenitor cell production are the cultures exchanged 3.5 times per week and inoculated at $5 \cdot 10^6$ cells/ml. These cultures produced a significant number of progenitor cells until week 20. Statistical analysis, using a paired t-test, showed that the optimum medium exchange rate cultures of 3.5/wk produced significantly more granulocyte-macrophage progenitor cells after week 8 than did the corresponding 7/wk and 1/wk cultures at all three inoculation densities at the 1% level of significance. The number of progenitor cells produced is important as it is an indirect measure of stem cell renewal. Progenitor cells can only be present after several weeks in culture by differentiation from an earlier cell, presumably a stem cell, which is still present in culture. Thus, these data suggest that more physiologic, rapid medium/serum exchange rate and higher cell densities may have provided conditions that supported some degree of stem cell renewal for five months.

Nonadherent cell morphology: To determine whether the prolonged hematopoiesis supported by the 3.5/wk cultures was qualitatively different from the other cultures, the nonadherent cells collected between weeks 10 and 19 were stained and typed morphologically. At the exchange rates of 1/wk and 7/wk, the cells produced were mostly macrophages by week 15 and thereafter (Table 2), which is similar to results from studies in other laboratories. In contrast, the cultures perfused at a rate of 3.5 medium volumes per week and seeded at $5 \cdot 10^6$ cells/ml produced granulocytes as well as macrophages through week 19. Thus, it seems that this medium exchange rate and inoculum density more effectively reconstituted granulopoiesis in vitro.

vivo, more effective reconstitution of bone marrow ex vivo can be attained.

Physical appearance: The medium exchange rate significantly affected the physical appearance of the cultures. By 10 weeks in culture, the 7/wk cultures had large number of adipose cells in the stroma while the 3.5/wk cultures had few fat cells and the 1/wk cultures never developed fat cells. At culture termination at 26 weeks, the stroma of the 7/wk cultures were composed of approximately 20–30% fat cells while the 3.5/wk cultures still only had a few fat cells. Adherent colony distribution also varied between cultures with different medium perfusion rate. Adherent colonies in the 3.5/wk cultures persisted longer than those in the 7/wk and 1/wk cultures.

TABLE 1

The average number of nonadherent progenitor cells removed from long term bone marrow cultures (LTBMCs) as a function of the medium perfusion rate and inoculum density.

| Week | 7/wk $5 \times 10^6$ per ml | 7/wk $2 \times 10^6$ per ml | 7/wk $1 \times 10^6$ per ml | 3.5/wk $5 \times 10^6$ per ml | 3.5/wk $2 \times 10^6$ per ml | 3.5/wk $1 \times 10^6$ per ml | 3.5/wk $5 \times 10^6$ per ml | 1/wk $2 \times 10^6$ per ml | 1/wk $1 \times 10^6$ per ml |
|---|---|---|---|---|---|---|---|---|---|
| 2 | 237 ± 27 | 11 ± 3.3 | 106 ± 5 | 120 ± 16 | 132 ± 7.9 | 167 ± 13 | 368 ± 29 | 94 ± 20.8 | 335 ± 46 |
| 4 | 149 ± 21 | 101 ± 5.1 | 104 ± 10 | 93 ± 10 | 37 ± 5.6 | 20 ± 0 | 21 ± 1.3 | 2 ± 0 | 8 ± 4.4 |
| 6 | 47.7 ± 7 | 12 ± 2.5 | 8 ± 0 | 17 ± 3 | 6 ± 4.1 | 5 ± 2.7 | 13 ± 5.1 | 1 ± 0 | 1 ± 0 |
| 8 | 40 ± 3 | 0 | 4 ± 0 | 38 ± 6 | 24 ± 2.7 | 10 ± 3 | 34 ± 7.4 | 0 | 0 |
| 10 | 0 | 0 | 0 | 28 ± 8.3 | 10 ± 2.9 | 5 ± 1.3 | 8 ± 2.3 | 2 ± 2.3 | 0 |
| 12.5 | 0 | 6 ± 2.3 | 0 | 8 ± 2.3 | 0 | 0 | 0 | 0 | 0 |
| 14 | 0 | 0 | 0 | 22 ± 6.4 | 6 ± 1.3 | 2.5 ± 1.2 | 3 ± 1.3 | 0 | 0 |
| 16 | 6 ± 2.2 | 0 | 0 | 24 ± 7.6 | 4 ± 1.7 | 2 ± 1.3 | 9 ± 3.6 | 0 | 0 |
| 18 | 0 | 0 | 0 | 24 ± 6.3 | 4 ± 1.3 | 0 | 0 | 0 | 0 |
| 20 | 0 | 0 | 0 | 5 ± 0 | 4 ± 0 | 3 ± 0 | 1 ± 0 | 0 | 0 |
| 22 | 2 ± 1.3 | 0 | 0 | 4 ± 1.3 | 10 ± 3 | 0 | 0 | 0 | 0 |
| 10–22* | 8 ± 3.5 | 6 ± 2.3 | 0 | 115 ± 32.2 | 40 ± 11.2 | 12.5 ± 3.8 | 21 ± 7.2 | 2 ± 7 | 0 |

Replicate samples at each medium perfusion rate and inoculum density were pooled and are each tabulated as one mean ± SEM.
*Cumulative CFU-GM production after week 8 is statistically greater in the 3.5/wk cultures than the corresponding cultures perfused at 7/wk or 1/wk at all inoculum densities at the 1% level of significance.

This result supports the hypothesis that long-term human Dexter culture conditions are suboptimal and as a culture in vitro better approximate the hematopoietic environment in

TABLE 2

Nonadherent cell morphology as a function of the medium perfusion rate and inoculum density.

| Medium perfusion rate | weeks | 5 × 10⁶ per ml | | | 2 × 10⁶ per ml | | | 1 × 10⁶ per ml | | |
|---|---|---|---|---|---|---|---|---|---|---|
| | | % Mφ | % G | % myeloid precursors | % Mφ | % G | % myeloid precursors | % Mφ | % G | % myeloid precursors |
| 7/wk | 10.4 | 25 | 57 | 18 | 57 | 32 | 11 | 52 | 34 | 14 |
| | 13.4 | 49 | 34 | 17 | 92 | 5 | 3 | 63 | 22 | 15 |
| | 15.4 | 66 | 19 | 16 | 79 | 19 | 2 | 54 | 17 | 29 |
| | 19 | 93 | 5 | 1 | 96 | 3 | 1 | 100 | 0 | 0 |
| 3.5/wk | 10.4 | 50 | 27 | 23 | 45 | 38 | 17 | 39 | 45 | 17 |
| | 13.4 | 23 | 59 | 19 | 27 | 56 | 17 | 36 | 47 | 17 |
| | 15.4 | 41 | 38 | 21 | 44 | 27 | 29 | 67 | 13 | 21 |
| | 19 | 58 | 37 | 5 | 88 | 9 | 3 | 99 | 1 | 0 |
| 1/wk | 10.4 | 59 | 21 | 20 | 60 | 11 | 29 | ND | ND | ND |
| | 13.4 | 56 | 25 | 20 | 19 | 36 | 46 | 43 | 7 | 50 |
| | 15.4 | 76 | 4 | 20 | ND | ND | ND | 46 | 39 | 15 |
| | 19 | 100 | 0 | 0 | 100 | 0 | 0 | 100 | 0 | 0 |

Data for pooled replicate samples at each medium perfusion rate and inoculum density and are shown as the percentage of macrophages (% Mφ), granulocytes (mature granulocytes and bands, % G), and immature granulocytes (metamyelocytes and less mature cells, % myeloid precursors).

Medium Replacement Combined with Supplementation of

Medium with Hematopoietic Growth Factors

Materials and Methods:

Cells: Human bone marrow cells were obtained following informed consent from heparinized aspirates of the iliac crest bone marrow, under a protocol approved by the University of Michigan Human Investigation Committee. The bone marrow was separated by a Ficoll-Paque (Pharmacia) density gradient centrifugation and the low density cells ($<1.077 gm/cm^3$) were collected and washed 3 times with IMDM. The cells were counted between the second and third washes. The cells were then seeded onto 6-well tissue culture plates (Costar No. 3406) or collagen coated 6-well plates (rat tail type 1 collagen, Biocoat. Collaborative Research Inc. Cat. No. 40400) in duplicate $5 \cdot 10^6$ cells/ml at 1.5 ml/well.

Culture medium: The medium used was IMDM (Gibco Laboratories. Cat. No. 430-2200) containing 10% fetal calf serum (Hyclone Laboratories), 10% horse serum (Hyclone Laboratories), 1% penicillin/streptomycin (Sigma, 10,000 U/ml penicillin G and 10 mg/ml streptomycin, Cat. No. P3539), and $10^{-5}M$ hydrocortisone (17-Hydroxycorticosterone, Sigma, Cat. No. H0888).

Hematopoietic growth factors (HGH): Due to the frequent culture supplementation via rapid medium exchange, hematopoietic growth factors were added to the medium at approximately 1/20 of the concentrations found to promote maximal colony formation in clonal assays 4. The concentrations used were 1 ng/ml of IL-3, 1 ng/ml of GM-CSF (Amgen Biologicals, Cat. No. 13050), 0.1 U/ml of Epo (Terry Fox Labs. Vancouver, Canada).

Hematopoietic progenitor cell assay: Nonadherent hematopoietic cells removed from culture were counted and plated at $1 \cdot 10^5$ cells/ml or fewer cells in methylcellulose. GM-CSF and Epo were added to the methylcellulose at 20 ng/ml and 2 U/ml, respectively. The cell were plated in 24 well plates at 0.25 ml/well and incubated at 37° C. for 14 days. The colonies were then counted under an inverted microscope and colonies greater than 50 cells were scored as GM-colony forming units (CFU-GM), erythroid burst-forming unit (BFU-E), or granulocyte erythroid megakaryocyte macrophage-colony forming unit (CFU-GEMM).

LTBMC conditions: The cultures were incubated at 37° C. in a humidified 5% $CO_2$/95% air atmosphere and perfused (medium exchanged) at a rate of 50% daily medium exchange. During the first week in culture, all cells removed during the daily medium exchange were centrifuged and returned to the original wells. After the first week in culture, 50% of the total nonadherent cells were removed from the cultures on a biweekly basis during the medium exchange, mononucleated cells counted, and fresh medium returned to the wells. The remaining five days per week when the cells were not counted, 50% of the medium was removed from each of the culture wells and replaced with fresh medium, the removed medium was centrifuged, the medium decanted from the cell pellet, and the cells returned to their original wells.

Statistical analysis: The probability of significant differences between groups of cultures was determined by comparing the normalized cumulative cell production values from the rapidly perfused cultures supplemented with hematopoietic growth factors to the matched untreated control cultures using a paired t-test. Statistical significance was taken at the 5% level. There were no statistical differences between matched rapidly perfused LTBMCs cultured on tissue culture plastic and type I rat tail collagen at the 5% level. Therefore, the data for the plastic and collagen matrix were combined for presentation in this and all other figures and statistical analysis performed on the combined data.

Results:

Kinetics of cell production in rapidly exchanged growth factor supplemented LTBMCs: As a first test of the hypothesis that the longevity and productivity of long term bone marrow cultures (LTBMCs) is limited by insufficient production of HGF's, we maintained rapidly exchanged ex vivo bone marrow cultures that were supplemented with IL-3, or Epo. In these cultures, 50% of the medium was removed daily and replaced with an equal volume of fresh medium supplemented with IL-3 or Epo. The cells removed were then centrifuged, the medium decanted and discarded, the cells resuspended, and the cells returned to the original cultures. IL-3 and Epo individually enhanced the cell productivity of rapidly exchanged LTBMCs. The cultures containing Epo alone initially had a high cell production rate due to substantial terminal erythroid differentiation. However, by week four erythropoiesis had ceased and the cell production rate had decreased to the level of the control cultures. IL-3 and Epo induced an average increase in nonadherent cell production over controls throughout the 18 weeks of culture of 175% and 173%, respectively.

Combinations of growth factors proved to be more effective in increasing the nonadherent cell production rate. The highest rate of cell production was observed for the combination of IL-3+GM-CSF+Epo. These cultures produced approximately 25% of the number of cells inoculated biweekly during the first 6 weeks in culture and had an average 4.8-fold increase in nonadherent cell production over controls during weeks 2–8. The combination of IL-3+GM-CSF produced an average 3.5-fold increase in nonadherent cells as compared to controls through week 8. In separate experiments, adding neither IL-6 nor G-CSF to the combination of IL-3+GM-CSF+Epo improved the nonadherent cell production rate, but instead resulted in cell production rates indistinguishable from the cultures containing the combination of IL-3+GM-CSF. In all cases, the stimulatory effect on cell production induced by the addition of HGFs was maximal between weeks 0 to 8, although cell production was higher than the controls throughout the culture.

The combinations of HGFs lead to high absolute numbers of nonadherent cells produced in rapidly exchanged LTB-MCS. The productivity of the cultures can be shown by comparing the cumulative number of cells produced over time ($\Sigma^n_{i=1} C_i$, $C_i$ being the number of nonadherent cells collected at time i), relative to the number of cells inoculated ($C_o$) by plotting the ratio ($\Sigma^n_{i=1} C_i, C_o$) as a function of time. When this ratio exceeds unity, a culture has produced more cells than were inoculated and the culture has led to an expansion in cell number.

The combination of IL-3+GM-CSF+Epo induced cumulative cell production that was more than 3-fold greater than the number of cells inoculated. The cell production rate was the highest during the first 6 weeks in culture during which time the culture produced approximately as many cells as were inoculated every two weeks. This maximum cell production rate was 15% of the estimated in vivo bone marrow cell production rate where 50% of the myeloid cell mass is generated daily. The combination of IL-3+GM-CSF resulted in more than a 2-fold expansion in cell number and at rates comparable to the combination of IL3+GM-CSF+Epo during weeks 3–7 in culture. Untreated rapidly exchanged (50% daily medium exchange) and slowly exchanged (50% medium exchange biweekly) control cultures not supplemented with HGFs produced approximately 1 and 0.37 times the number of cells inoculated after 18 weeks, respectively. More importantly more than half of all cells removed from these unsupplemented cultures came from the first two samplings, indicating that many of these cells were from the original inoculum and that supplementation of the cultures with HGFs are required to induce significant cycling of progenitor and stem cells.

Morphologic analysis of nonadherent cells: The addition of multiple HGFs also increased the variety of myeloid cells produced in the cultures. The control cultures produced nonadherent cells that were predominately macrophages after week 3 in the culture. Production of erythroid cells decreased rapidly with few erythroid cells detected after week 5. The cultures containing Epo (Epo alone, IL-3+Epo, and IL-3+GM-CSF+Epo) produced a transient increase in erythroid cell production, with a high percentage (55–75%) of nonadherent cells being erythroid through week 3. When IL-3+Epo±GM-CSF was present, the cultures continued to produce erythroid cells throughout the 16 weeks in culture with about 5–15% of the nonadherent cells being typed as erythroid. Thus, in the presence of IL-3+Epo, erythropoiesis was active throughout.

IL-3±Epo led to a nonadherent cell population that was predominately (60–70%) late granulocytes (LG) at week 5. The percentage of LGs steadily declined until it reached about 20% at week 18. The production of macrophages rose correspondingly. When GM-CSF was added to IL-3±Epo, the high percentage of LG persisted through 18 weeks. The combination of IL-3+GM-CSF thus led to active granulopoiesis for 18 weeks in culture, and the addition of Epo maintained erythropoiesis as well. Photomicrographs of the control and IL-3+GM-CSF+Epo supplemented cultures at 5.5 weeks in culture show the dramatic enhancement in culture density and variety of cells produced.

Kinetics of nonadherent progenitor cell production: Progenitor cell production increased with the addition of multiple HGFs. The production of granulocyte macrophage colony forming units (CFU-GMs) in the untreated controls was prolonged and steady for over 18 weeks, which is consistent with the earlier results obtained using rapidly perfused LTBMC without HGF. CFU-GM produced in the IL-3+GM-CSF and IL-3+Epo±GM-CSF cultures was approximately 10-fold higher than controls during weeks 3 to 5.

Erythroid burst forming unit (BFU-E) production in human LTBMC has been reported to be low and cease quickly (*Coutinho et al, Blood* (1990) 75(11): 2118–2129). The rapidly exchanged, untreated controls exhibited a rapid decrease in BFU-E production although low levels of BFU-E were produced through 17 weeks in culture. The addition of Epo alone did not significantly influence the number of BFU-Es produced. IL-3 alone induced a mild short-lived stimulation of BFU-E production in weeks 3–5. On the other hand, IL-3 plus either Epo or GM-CSF induced a 10 to 20-fold elevation of nonadherent BFU-E levels compared to that of controls during weeks 3 to 5 of culture.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An ex vivo cell culture composition comprising human stem cells found in the human hematopoietic system, cultured in a liquid culture medium which is replaced at a rate which is substantially continuous and provides ex vivo human stem cell division, wherein said human stem cells are rendered mitotic ex vivo.

2. The composition of claim 1, further comprising cultured mitotic human progenitor cells found in the human hematopoietic system.

3. The ex vivo mitotic human stem cell culture composition of claim 1 comprising Epo.

4. The ex vivo mitotic human stem cell culture composition of claim 1 comprising IL-3.

5. The ex vivo mitotic human stem cell culture composition of claim 1 comprising GM-CSF.

6. The ex vivo mitotic human stem cell culture composition of claim 1 comprising G-CSF.

7. The ex vivo mitotic human stem cell culture composition of claim 1 comprising IL-6.

8. The ex vivo mitotic human stem cell culture composition of claim 1 comprising IL-11.

9. The ex vivo mitotic human stem cell culture composition of claim 1 comprising steel factor.

10. The ex vivo mitotic human stem cell culture composition of claim 1 comprising at least one member selected from the group consisting of Epo, IL-3, GM-CSF, G-CSF, IL-6, IL-11 and Stem Cell Factor.

11. The ex vivo mitotic human stem cell culture composition of claim 1 comprising IL-7.

12. A cellular composition obtained by culturing cellular composition comprising human stem cells found in the human hematopoietic system in a liquid culture medium which is replaced at a rate which is substantially continuous and provides exvivo human stem cell division, while maintaining said culture under physiologically acceptable conditions.

13. The cellular composition of claim 12, wherein said liquid culture medium is replaced at a rate of at least 50% daily replacement.

14. The cellular composition of claim 12, wherein said liquid culture medium is replaced at a rate of from 50 to 100% daily replacement.

15. The cellular composition of claim 12, wherein said liquid culture medium is replaced at a rate related to the cell density of the culture, said rate being equal to a rate of from 50 to 100% daily replacement for a cell density of from $1\times10^4$ to $1\times10^7$ cells per ml of culture.

16. The cellular composition of claim 12, further comprising human stromal cells.

17. A cell composition obtained by culturing a cellular composition comprising (i) human hematopoietic stem cells or (ii) human bone marrow cells, in a liquid culture medium which is replaced at a rate which is substantially continuous and provides ex vivo human stem cell division therein while maintaining said culture under physiologically acceptable conditions.

18. The cellular composition of claim 17, wherein said liquid culture medium is replaced at a rate of at least 50% daily replacement.

19. The cellular composition of claim 17, wherein said liquid said culture medium is replaced at a rate of 50 to 100% daily replacement.

20. The cellular composition of claim 17 wherein said liquid culture mediums is replaced at a rate related to the cell density of the culture, said rate being equal to a rate of from 50 to 100% daily replacement for a cell density of from $1\times10^4$ to $1\times10^7$ cells per ml of culture.

21. The human bone marrow composition of claim 17, wherein said (i) human hematopoietic stem cell culture further comprises human stromal cells.

22. The human bone marrow composition of claim 17, obtained by culturing human hematopoietic stem cells.

23. The human bone marrow composition of claim 17, obtained by culturing human bone marrow cells.

24. A method of using a human bone marrow composition according to claim 17, comprising using said composition in an autologous or an allogenic human bone marrow transplantation.

25. In an autologous or an allogeneic human bone marrow transplantation, the improvement comprising using a cell composition obtained by culturing (i) human bone marrow cells or (ii) a cellular composition comprising human hematopoietic stem cell in a liquid culture medium which is replaced at a rate which is substantially continuous and provides ex vivo human stem cell division therein, while maintaining said culture under physiologically acceptable conditions.

26. The cellular composition of claim 25, wherein said liquid culture medium is replaced at a rate of at least 50% daily replacement.

27. The cellular composition of claim 25, wherein said liquid culture medium is replaced at a rate of from 50 to 100% daily replacement.

28. The cellular composition of claim 25 wherein said liquid culture medium is replaced at a rate related to the cell density-of the culture, said rate being equal to a rate of from 50 to 100% daily replacement for a cell density of from $1\times10^4$ to $1\times10^7$ cells per ml of culture.

29. An autologous human bone marrow transplantation in accordance with claim 25.

30. An allogeneic human bone marrow transplantation in accordance with claim 25.

31. The bone marrow transplantation of claim 25, comprising culturing human bone marrow cells.

32. The bone marrow transplantation of claim 25, comprising culturing human hematopoietic stem cells.

33. The bone marrow transplantation of claim 25, wherein said human hematopoietic stem cell culture further comprises human stromal cells.

34. A cell composition for use in human blood transfusions obtained by culturing a cellular composition comprising (i) human hematopoietic stem cells or (ii) human hematopoietic cells, in a liquid culture medium which is replaced at a rate which is substantially continuous and provides ex vivo human stem cell division therein, while maintaining said culture under physiologically acceptable conditions.

35. The cellular composition of claim 34, wherein said liquid culture medium is replaced at a rate of at least 50% daily replacement.

36. The cellular composition of claim 34 wherein, said liquid culture medium is replaced at a rate of from 50 to 100% daily replacement.

37. The cellular composition of claim 34, wherein said liquid culture medium is replaced at a rate related to the cell density of the culture, said rate being equal to a rate of from 50 to 100% daily replacement for a cell density of from $1\times10^4$ to $1\times10^7$ cells per ml of culture.

38. The human blood transfusion composition of claim 34, wherein said human hematopoietic stem cell culture further comprises human stromal cells.

39. A method of using a human blood transfusion composition according to claim 34, comprising transfusing said composition into a human patient in need thereof.

40. A human cell culture composition comprising cultured mitotic human stem cells found in the human hematopoietic system and an expanded population of human progenitor cells found in the human hematopoietic system obtained by culturing a cellular composition comprising human stem cells found in the human hematopoietic system in a liquid culture medium which is replaced at a rate which is substantially continuous and provides ex vivo human stem cell division and human progenitor cell expansion therein, while maintaining said culture under physiologically acceptable conditions.

41. A cellular composition obtained by culturing human progenitor cells found in the human hematopoietic system in a liquid culture medium which is replaced at a rate related to the cell density of the culture to thereby obtain expansion of said human progenitor cellA, said rate being equal to a rate of from 50 to 100% daily replacement for a cell density of from $1\times10^4$ to $1\times10^7$ cells per ml of culture, while maintaining said culture under physiologically acceptable conditions.

42. The cellular composition of claim 41, wherein said liquid culture medium is replaced at a rate of at least 50% daily replacement.

43. The cellular composition of claim 41, wherein said liquid culture medium is replaced at a rate of from 50 to 100% daily replacement.

44. A cell culture composition comprising mitotic human stem cells, wherein said composition is obtained by culturing cells derived from human bone marrow in a liquid culture medium which is replaced at a rate which is substantially continuous and provides ex vivo human stem cell division.

45. An ex vivo cell culture composition in which a substantial number of human stem cells originating from a human hematopoietic system have undergone ex vivo cell division as a result of the conditions in a medium-exchange ex vivo culture.

46. An ex vivo human hematopoietic or stromal stem cell composition in which a substantial number of human hematopoietic or stromal stem cells have undergone ex vivo cell division as a result of the conditions in a medium-exchange ex vivo culture.

47. An ex vivo human bone marrow stem cell composition in which a substantial number of human bone marrow stem cells have undergone ex vivo cell division as a result of the conditions in a medium-exchange ex vivo culture.

48. The ex vivo human stem cell composition of claim 45, further comprising human progenitor cells originating from a human hematopoietic system having undergone ex vivo cell division as a result of the conditions in said medium-exchange ex vivo culture.

49. The ex vivo human hematopoietic stem cell composition of claim 45, further comprising human hematopoietic progenitor cells having undergone ex vivo cell division as a result of the conditions in said medium-exchange ex vivo culture.

50. The ex vivo human stromal stem cell composition of claim 45, further comprising human stromal lineage cells having undergone ex vivo cell division as a result of the conditions in said medium-exchange ex vivo culture.

51. The ex vivo human bone marrow stem cell composition of claim 47, further comprising human bone marrow progenitor cells having undergone ex vivo cell division as a result of the conditions in said medium-exchange ex vivo culture.

\* \* \* \* \*